US00PP08037P

United States Patent [19]

Wuhl

[11] Patent Number: Plant 8,037

[45] Date of Patent: Nov. 24, 1992

[54] 'SHOWTIME' PLUM TREE

[76] Inventor: Eric Wuhl, 5480 E. Lane Ave., Fresno, Calif. 93727

[21] Appl. No.: 719,760

[22] Filed: Jun. 24, 1991

[51] Int. Cl.[5] ..... A01H 5/00

[52] U.S. Cl. ..... Plt./38.1

[58] Field of Search ..... Plt. 38.1

*Primary Examiner*—James R. Feyrer

*Attorney, Agent, or Firm*—Worrel & Worrel

[57] ABSTRACT

A new and distinct variety of plum tree which is somewhat remotely similar to the "Santa Rosa" plum tree (unpatented) from which it was derived, but from which it is distinguished by producing uniformly larger fruit which are mature for harvesting and shipment approximately the same time as that of the "Santa Rosa" plum tree but which exhibit a superior holding ability, as compared with that of the "Santa Rosa" plum tree and having a generally redder flesh coloration.

1 Drawing Sheet

BACKGROUND OF THE NEW VARIETY

The present invention relates to a new and distinct variety of plum tree, which will hereinafter be denominated varietally as the "Showtime" plum tree, and more particularly to a plum tree which produces fruit which are mature for commercial harvesting and shipment approximately contemporaneously with the "Santa Rosa" plum tree (unpatented), or about June 18 to about June 25 in the San Joaquin Valley of central California, and which further is distinguished principally as to novelty by producing uniformly larger fruit which have redder flesh than that of the "Santa Rosa" plum tree, a red to purple skin coloration, and which can hold on the tree and stay firm to a significantly higher level of maturity.

The "Santa Rosa" plum tree has been one of the most commercially successful varieties of plum tree over many decades producing large fruit having pleasingly colored and flavorful flesh ripening for harvest approximately June 18 in the San Joaquin Valley of central California. There have been many commercially successful progeny of the "Santa Rosa" plum tree, but the "Santa Rosa" plum tree remains in many respects the standard by which other varieties are judged.

However, the "Santa Rosa" plum tree has some traits which are less than desirable. For example, the "Santa Rosa" plum tree is frequently characterized by premature fruit drop which makes harvesting a particularly critical operation and, of course, reduces the volume of the crop which can successfully be harvested.

The "Showtime" plum tree of the present invention possesses many of the same attractive characteristics of the "Santa Rosa" plum tree producing fruit of red to purple skin coloration ripening for harvest approximately June 18 to June 25. However, the fruit of the instant variety is uniformly larger and has flesh of a consistently redder coloration. It is further distinguished from the "Santa Rosa" plum tree in that the fruit of the "Showtime" plum tree consistently holds on the tree and remains firm considerably longer than that of the "Santa Rosa" plum tree.

ORIGIN AND ASEXUAL REPRODUCTION OF THE NEW VARIETY

The present variety of plum tree was discovered by the inventor in 1983 as an open field, cross pollinated hybrid of the Santa Rosa plum tree. The parent plum tree of the new variety was discovered in his orchard which is located at 5480 E. Lane Avenue, Fresno, Calif.

The new variety was asexually reproduced by the inventor in 1986 by grafting scions of the new variety onto rootstock in an orchard of plum trees located one quarter mile east of Clovis, Calif. The inventor has observed the progeny of the new variety through the growing seasons since 1986 and confirmed that the distinctive characteristics of the parent tree are precisely reproduced in the progeny.

SUMMARY OF THE NEW VARIETY the "Showtime" plum tree is characterized as to novelty by producing a large fruit generally of a red to purple skin coloration ripe for commercial harvesting and shipment approximately June 18 to June 25 in the San Joaquin Valley of central California. The new and novel variety is most closely similar to the "Santa Rosa" plum tree (unpatented) from which it was derived as a newly found seedling, but from which it is distinguished and characterized principally as to novelty by producing uniformly larger fruit having a generally redder flesh coloration and having a significantly superior holding ability avoiding the premature fruit drop characteristic of the "Santa Rosa" plum tree.

BRIEF DESCRIPTION OF THE DRAWING

The drawing is a color photograph showing mature fruit of the new variety of plum tree of the present invention including a first shown in top plan view showing thereof the apex; a second shown in bottom plan view showing the base thereof; a third shown in side elevation; a fourth sectioned along the suture plane with the stone left in place; and a fifth sectioned along the suture plane with the stone removed to expose the pit cavity; a representative leaf shown in top plan view, a second leaf shown in bottom plan view; and a representative section of a twig, all of the new variety.

DETAILED DESCRIPTION

Referring more specifically to the pomological details of this new and distinct variety of plum tree, the following has been observed under the ecological conditions prevailing at the orchard of origin which is located near Fresno in the San Joaquin Valley of central California. All major color code designations are by reference to the *Dictionary of Color*, by Maerz and Paul, Second Edition, 1950. Common color names are also occasionally employed.

TREE

Generally:
- *Size.*—Medium.
- *Figure.*—Upright.
- *Productivity.*—Productive.
- *Regularity of bearing.*—Regular.

Trunk:
- *Size.*—Stocky.
- *Surface texture.*—Medium.

Branches:
- *Size.*—Medium.
- *Surface texture.*—Medium, shaggy.
- *Color.*—Page 33, Plate 5, D-9 Roseglow.
- *Lenticels.*—Numbers — Numerous. Size — 0.5 mm (0.0019 inches) to 1 mm (0.039 inches) by 2 mm (0.078 inches) to 5 mm (0.196 inches).

LEAVES

Size:
- *Generally.*—Small to Medium.
- *Average length.*—85 mm (3.346 inches) to 90 mm (3.543 inches).
- *Average width.*—35 mm (1.377 inches) to 40 mm (1.574 inches).

Shape: Ovate.

Marginal form: Double Serrate.

Color:
- *Upwardly disposed surface.*—Page 67, Plate 22, H-8, Civette Gr.
- *Downwardly disposed surface.*—Page 63, Plate 20, C-6, Seaspray T.

Glandular characteristics: None.

Petiole:
- *Length.*—10 mm (0.393 inches) to 12 mm (0.472 inches).
- *Thickness.*—2 mm (0.078 inches).

Stem glands:
- *Form.*—Globose.
- *Size.*—Small.
- *Number.*—Two to Eight.
- *Position.*—Opposite.
- *Color.*—Green.

Stipules: None.

FLOWERS

Flower buds:
- *Size.*—4 mm (0.157 inches).
- *Surface texture.*—Glabrous.

Flowers:
- *Generally.*—Small.

Date of bloom: February 21.

Size:
- *Generally.*—15 mm (0.590 inches) to 20 mm (0.787 inches) when open.

Petals:
- *Color.*—White.

Pistil: One

Stamen:
- *Number.*—28 to 32.

FRUIT

Maturity when described: Ripe for commercial harvesting and shipment approximately June 18 to June 25 in the San Joaquin Valley of central California.

Size:
- *Generally.*—Uniform.
- *Average diameter.*—58 mm (2.283 inches) to 62 mm (2.440 inches).
- *Average diameter transverse in the suture plane.*—54 mm (2.125 inches) to 61 mm (2.401 inches).
- *Average diameter transverse and at right angles to the suture plane.*—52 mm (2.047 inches) to 57 mm (2.244 inches).
- *Form.*—Uniformity — Uniform.
- *Suture.*—Length — 87 mm (3.425 inches) to 100 mm (3.937 inches). Position — Inconspicuous line.
- *Ventral surface.*—Generally — Smooth.
- *Stem cavity.*—Generally — Acute. Width — 16 (0.629 inches). Depth — 10 mm (0.393 inches). Length — 22 mm (0.866 inches).
- *Stem.*—Length — 12 mm (0.472 inches). Caliper — 22 mm (0.866 inches).
- *Base.*—Flat.
- *Apex.*—Shape — Slightly pointed.
- *Pistil point.*—Position — Variable.

Skin:
- *Thickness.*—Thin.
- *Texture.*—Medium.
- *Tendency to crack.*—None.
- *Color.*—Page 33, Plate 5, C-6 Afgan R Cheekerberry.
- *Pubescence.*—None.

Flesh:
- *Flesh color.*—Near apex — Page 33, Plate 5, C-6, Afgan R (Asskin). Remainder — Page 41, Plate 9, E-5, Capucine Buff.
- *Surface of pit cavity.*—Smooth.
- *Color of pit well.*—Page 41, Plate 9, E-5.
- *Amygdalin.*—None.
- *Juice production.*—Juicy.
- *Flavor.*—Pleasant.
- *Aroma.*—Wanting.
- *Texture.*—Meaty.
- *Fibers.*—Numbers — Few.
- *Ripening.*—Even.
- *Eating quality.*—Good.

Stone
- *Attachment.*—Freestone.
- *Fibers.*—Numbers — None.
- *Size.*—Length — 21 mm (0.826 inches). Width — 15 mm (0.590 inches). Thickness — 8 mm (0.314 inches).
- *Form.*—Generally — Oval.
- *Color.*—Page 41, Plate 9, E-5.
- *Base.*—Shape — Flat.
- *Sides.*—Generally — Equal.
- *Ridges.*—Rounded.
- *Size of position of grooves.*—None.
- *Dorsal edge.*—Smooth.
- Ventral edge.—Wing in middle of pit.
- *Tendency to split.*—None.

Use: Fresh.

Keeping quality: Good.

Resistance to disease: Usual disease characteristic to be expected.

Shipping and handling qualities: Good.

Although the new variety of tree possesses the described characteristics noted above as a result of the growing conditions prevailing near Fresno in the central part of the San Joaquin Valley of central California, it is to be understood that variations of the usual magnitude and characteristics incident to changes in growing conditions, irrigation, fertilization, pruning and pest control are to be expected.

Having thus described and illustrated my new variety of nectarine tree, what I claim as new and desire to be secured by Plant Letters Patent is:

1. A new and distinct variety of plum tree substantially as illustrated and described and which is somewhat remotely similar to the "Santa Rosa" plum tree (unpatented) from which it was derived and with which it is most clearly similar, but from which it is distinguished and characterized principally as to novelty by producing uniformly larger fruit which have a generally redder flesh coloration and which are mature for commercial harvesting and shipment approximately June 18 to June 25 in the San Joaquin Valley of central California and which further has noteworthy holding, shipping and handling characteristics.

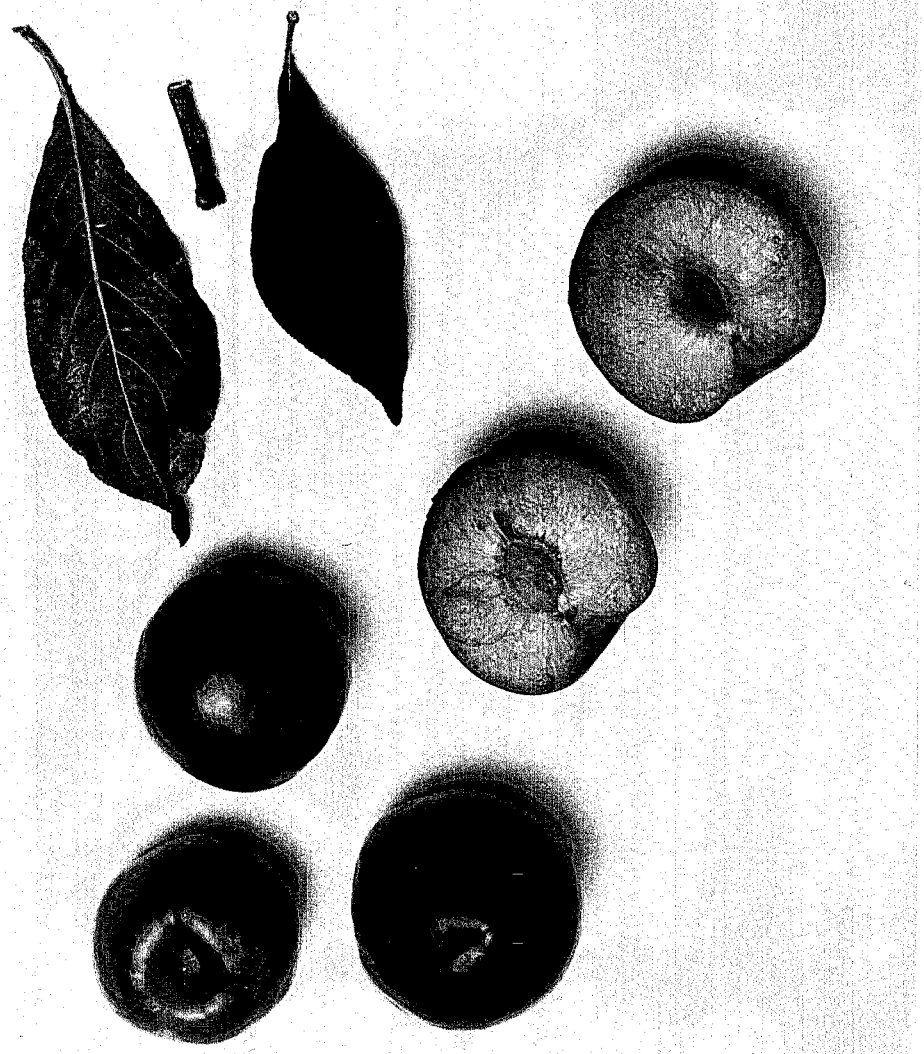

* * * * *